United States Patent
Gilljam et al.

(10) Patent No.: US 9,296,799 B2
(45) Date of Patent: Mar. 29, 2016

(54) PROCESS FOR ISOLATION AND PURIFICATION OF A TARGET PROTEIN FREE OF PRION PROTEIN (PRP$^{SC}$)

(75) Inventors: Gustav Gilljam, Skogas (SE); Mats Jernberg, Stockholm (SE); Stefan Winge, Arsta (SE); Andrea Neisser-Svae, Mödling (AT)

(73) Assignee: OCTAPHARMA AG, Lachen (CH)

( * ) Notice: Subject to any disclaimer, the term of this patent is extended or adjusted under 35 U.S.C. 154(b) by 611 days.

(21) Appl. No.: 12/733,306

(22) PCT Filed: Aug. 25, 2008

(86) PCT No.: PCT/EP2008/061068
§ 371 (c)(1),
(2), (4) Date: Apr. 20, 2010

(87) PCT Pub. No.: WO2009/024620
PCT Pub. Date: Feb. 26, 2009

(65) Prior Publication Data
US 2010/0210821 A1    Aug. 19, 2010

(30) Foreign Application Priority Data
Aug. 23, 2007 (EP) .................................. 07114856

(51) Int. Cl.
*C07K 14/47* (2006.01)

(52) U.S. Cl.
CPC ...................................... *C07K 14/47* (2013.01)

(58) Field of Classification Search
None
See application file for complete search history.

(56) References Cited

U.S. PATENT DOCUMENTS

2011/0160435 A1* 6/2011 Borgvall et al. .............. 530/383

FOREIGN PATENT DOCUMENTS

| CN | 1926146 | | 3/2007 | | |
|---|---|---|---|---|---|
| SE | WO 2005/082483 | * | 9/2005 | ............. | B01D 15/08 |
| SE | EP 1707634 | * | 4/2006 | ............. | C12P 21/02 |
| WO | 9408686 | | 4/1994 | | |
| WO | WO 94/08686 | | 4/1994 | | |
| WO | 9800441 | | 1/1998 | | |
| WO | WO 98/00441 | | 1/1998 | | |
| WO | 03105911 | | 12/2003 | | |
| WO | WO 03/105911 | | 12/2003 | | |
| WO | 2004024318 | | 3/2004 | | |
| WO | WO 2004/024318 | | 3/2004 | | |

OTHER PUBLICATIONS

Foster. Assessment of the potential of plasma fractionation processes to remove causative agents of transmissible spongiform encephalopathy. Transfus Med. Mar. 1999;9(1):3-14.*
Prusiner. Novel proteinaceous infectious particles cause scrapie. Science. Apr. 9, 1982;216(4542):136-44.*
Sowemimo-Coker. Making blood safe. The Biochemist—Aug. 2005. p. 29-32.*
Telling et al. Prion propagation in mice expressing human and chimeric PrP transgenes implicates the interaction of cellular PrP with another protein. Cell. Oct. 6, 1995;83(1):79-90. Abstract Only.*
Zeiler et al. "Concentration and removal of prion proteins from biological solutions." Biotechnology and Applied Biochemistry, vol. 37, No. 2, (Apr. 2003), pp. 173-182.
Brimacombe et al. "Characterization and polyanion-binding properties or purified recombinant prion protein." Biochemical Jouranl, vol. 342, (1999), pp. 605-613.
Burnouf et al. "Current strategies to prevent transmission of prions by human plasma derivatives." Transfusion Clinique et Biologique, vol. 13, No. 5, (Feb. 1, 2007), pp. 320-328.
Foster et al. "Studies on the removal of abnormal prion protein by processes used in the manufacture of human plasma products." Vox Sanguinis, vol. 78, No. 2, (Mar. 2000), pp. 86-95.
Pan et al. "Purification and properties of the cellular prion protein from Syrian hamster brain." Protein Science, vol. 1, (1992), pp. 1343-1353.
Thyer et al. "Prion-removal capacity of chromatographic and ethanol precipitation steps used in the production of albumin and immunoglobulins." Vox Sanguinis, vol. 91, No. 4 (2006), pp. 292-300.
Thyer et al. Prion-removal capacity of chromatographic and ethanol precipitation steps used in the production of alumbin and immunoglobulins, Vox Sanguins, vol. 91, issue 4, p. 292, Nov. 30, 2008.
Burnouf et al. Current strategies to prevent transmission to prions by human plasma derivatives. Transfusion Clinique et Biologique, vol. 13, issue 5, pp. 323-324, Table 2, Feb. 1, 2007.
Brimacombe D B. Characterization and polyanion-bingding properties of purified recombinant prion protein. Biochemical Journal, vol. 342, No. 3, pp. 606-608 Sep. 15, 1999.
Foster et al. Studies on the removal of abnormal prion protein by processes used in the manufacture of human plasma products. Vox Sanguinis, vol. 78, issued 2, p. 292, Mar. 31, 2000.
Pan et al. Purification and properties of the cellular prion protein from Syrian hamster brain. Protein Science, vol. 1, issue 10, Oct. 31, 1992.
Zeiler et al. Concentration and removal of prion proteins from biological solutions. Biotechnology and Applied Biochemistry, vol. 37, issue 2, pp. 173-182, Apr. 30, 2003.

* cited by examiner

*Primary Examiner* — Michelle S Horning
(74) *Attorney, Agent, or Firm* — Jacobson Holman PLLC

(57) ABSTRACT

A process for isolation and purification of a target protein by chromatography wherein the chromatography removes or depletes prions (PrP$^{SC}$), comprising the steps of contacting a potentially PrP$^{SC}$ contaminated sample comprising a target protein with a multimodal chromatographic material; setting buffer conditions so that the target protein is bound to the multimodal chromatographic material and whereas PrP$^{SC}$ is not binding to the multimodal chromatographic material; followed by elution of the target protein. a process for isolation and purification of a target protein free of prion protein (prp$^{SC}$).

4 Claims, No Drawings

PROCESS FOR ISOLATION AND PURIFICATION OF A TARGET PROTEIN FREE OF PRION PROTEIN (PRP$^{SC}$)

This is a 371 of PCT/EP08/061068 filed Aug. 25, 2008, which has a priority of European no. 07114856.3 filed Aug. 23, 2007, hereby incorporated by reference.

The Present Invention Pertains to a Process for Isolation and Purification of a target protein which is free of the disease associated protein form PrP$^{SC}$.

In recent times focus on PrP$^{SC}$ inactivation and removal in purification methods for blood plasma derived drugs, has been attributed increased attention. The reason obviously being the outbreak of mad cows diseases etc. Even the use of recombinant cell lines for production of biopharmaceutical drugs is not regarded as completely safe concerning the occurrence of prion proteins (Vorberg et al., The Journal of infectious diseases 2004; 189:431-9. Susceptibility of common fibroblast cell lines to transmissible spongiform encephalopathy agents). During the work to define a purification process for proteins intended as biopharmaceutical drugs, different purification steps can be evaluated as possible prion protein removal steps (Foster P R, et al; Distribution of a bovine spongiform encephalopathy-derived agent over ion-exchange chromatography used in the preparation of concentrates of fibrinogen and factor VIII; Vox Sang. 2004 February; 86(2):92-9; Trejo S R, et al, Evaluation of virus and prion reduction in a new intravenous immunoglobulin manufacturing process. Vox Sang. 2003 April; 84(3):176-87; Zeiler B, et al, Concentration and removal of prion proteins from biological solutions; Biotechnol Appl Biochem. 2003 April, 37 (Pt 2):173-82; Foster et al. Studies on the removal of abnormal prion protein by processes used in the manufacture of human blood plasma products, Vox Sang. 2000, 78:86-95; Burnouf et al., Transfus Clin Biol. 2006 November; 13 (5):320-8. Epub 2007 Jan. 23, Current strategies to prevent transmission of prions by human plasma derivatives.

Chromatography resins have been shown to be able to contribute to the removal of PrP$^{SC}$ in a purification process (reference 2-4, 6-7). However, it has been stated that the fact that consistent PrP$^{SC}$ clearance factors are found in processes using chromatographic resins of different chemical structure and substitutions and under different buffer systems, supports the occurrence of non-specific binding of the infectious agent onto the chromatographic support surface. Although PrP$^{SC}$ removal appears reproducible, incomplete understanding of the removal mechanism raises questions, such as how to (a) determine the maximum capacity of chromatographic support to bind TSE agents, (b) ensure efficient sanitizing procedures of recycled gels and (c) guarantee consistent PrP$^{SC}$ removal over production cycles (Thyer J, Prion-removal capacity of chromatographic and ethanol precipitation steps used in the production of albumin and immunoglobulins; Vox Sang. 2006 November; 91(4):292-300).

WO-A-98/0041 discloses removal of a prion from other proteins, e.g. haemoglobin, by ion exchange chromatography. The preparation of the ion exchange chromatographic medium reveal silica gel derivatizesed with (g-glycidoxypropyl)trimethoxysilane and dimethanolamine to obtain a (uniform) surface of quaternary ammonium groups.

WO-A-03/105911 discloses a cleaning method of human plasma by conventional means of ion exchange chromatography using a salt gradient for elution.

WO-A-94/08686 discloses a process for carrying out in a consecutive fashion different notes of chromatographic separation in a liquid chromatography column using a single separation medium.

D. B. Brimacombe et al. in Biochem. J. (1999) 342, 605-613 discloses the purification of recPrP by two successive chromatographic steps. The first step is a cation-exchange chromatography (150-650 NaCl-gradient) performed on S-Sepharose. The pooled eluates of interest were subjected to a second chromatographic step (zink charged chelating sepharose; 0-100 mM imidazole gradient).

P. R. Foster et al. Vox Sanguinis 2000; 78:86-95 discloses the removal of prion protein in the manufacture of plasma products by many steps. This method comprises 4 ion-exchange chromatographies (Steps 2, 11, 13 and 15) and one affinity chromatography (immobilised heparin on sepharose-FF; Step 12) performed in different columns on different chromatographic gels.

T. Burnouf et al. publishes in Tranfusion Clinique et Biologique 13 (2006) 320-328, the extent of TSE agent removal during various chromatographic steps of plasma derived coagulation factors. The publication focuses on various (mostly) ion-exchange chromatographic steps used in the production of FVIII (DEAE-Toyopearl 650M), vWF (DEAE-Toyopearl 650M), fibrinogen (DEAE-Toyopearl 650M), prothrombin complex/FIX (DEAE-cellulose), PCC (DEAE-Sepharose), FIX (DEAE-Sepharose or Heparin-Sepharose) and thrombin (S-Sepharose). All of these systems were investigated separately.

J. Thyer et al. in Vox Sanguinis (2006) 91, 292-300, reports on the reduction of PrP over DEAE-Sepharose, CM-Sepharose and Macro-Prep High Q chromatographic columns ("Materials and Methods"; FIG. 1, page 294; Table 1). In another experiment the sequential use of one DEAE-Sepharose-column and one CM-Sepharose- or Macro-Prep-column is disclosed.

SUMMARY OF THE INVENTION

One object of the invention was to provide a chromatographic process which removes PrP$^{SC}$ during fractionation processes of sources being potentially contaminated by PrP$^{SC}$, such as biologically derived sources. The process should avoid the drawbacks of prior art. Another object was to design a process which would render the purification process reliable and allowing regeneration of the chromatographic supports.

Still another object of the invention was to provide prion depleted fraction of proteins.

According to the invention a process for isolation and purification of a target protein by chromatography wherein the chromatography removes or depletes prions (PrP$^{SC}$) is provided comprising the steps of contacting a potentially PrP$^{SC}$-contaminated sample comprising a target protein with a multimodal chromatographic material;

setting buffer conditions so that the target protein is bound to the multimodal chromatographic material and PrP$^{SC}$ is not binding to the multimodal chromatographic material;

followed by elution of the target protein, and collecting the target protein.

The process of the invention provides a significant improvement because the chromatography resin binds the PrP$^{SC}$ less strong enabling removal of the PrP$^{SC}$ from the chromatography resin before the target protein is eluted.

According to the invention "isolation and purification" means in particular processes which are used to at least enrich any protein-like substances desired or processes which deplete unwanted substances. According to the invention it would be advantageous to yield the desired product as pure as possible.

The term "target protein" means a protein of interest which should be isolated and/or purified free of $PrP^{SC}$. The target protein can also be a still mixture of proteins if so desired e.g. a mixture of different factors having a biological effect when working in an ensemble.

"Prions" are infectious proteinaceous substances.

DETAILED DESCRIPTION OF THE INVENTION

Surprisingly it was found that a single chromatography resin has been able to minimize the binding of $PrP^{SC}$ to the gel under chromatography conditions and therefore achieving excellent reduction values for the product which binds to it. This resin is commercially available and described e.g in WO-A-2004/024318. The disclosure is incorporated by reference. The resin which has shown to have this effect towards $PrP^{SC}$ is called multi modal (or mixed mode or hydrophobic charged induction) resin. In opposite to, for example standard chromatography media like ion exchangers and hydrophobic interaction chromatography resins, which work through only one principle, multi modal resins work through a combination of ionic interactions and hydrophobic interactions. Examples of such resins are commercially available Capto® MMC and Capto® Adhere from the company GE Healthcare, or MEP, HEA or PPA Hypercel® resins from the company PALL. The ligands of these multimodal resins can be differently designed; examples of different ligands are the following 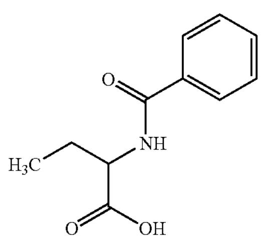 2-(benzoylamino)butanoic acid 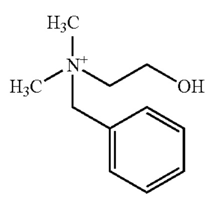 N-benzyl-2-hydroxy-N,N-dimethylethanaminium 3-({3-methyl-5-[(tetrahydrofuran-2-ylmethyl)amino]phenyl}amino)benzoic acid The kind of the multimodal chromatographic material is summarised in the following.

The present invention provides a solid substrate that is an effective adsorbent for use in separating and isolating a variety of biological substances. The solid substrate of this invention may be used, for example, in preparative techniques, such as column chromatography, and in analytical devices, such as biochips. One advantage of the present solid substrate described herein is its high selectivity and specificity for biological substances such as immunoglobulins, together with the avoidance of costly and often detrimental cleaning processes required for prior art substrates. A second advantage is that the solid substrate of this invention is almost ideally suited for use with biological samples at physiological pH and ionic strength, thereby obviating the need for pH adjustment and the addition of lyotropic salts as prescribed in the prior art. As third advantage may be regarded the high capacity of the present substrates, which, in view the low cost of reagents employed to prepare them, presents significant economic gains over the use of specialized prior art adsorbents.

Mixed Mode Ligand

The solid substrates of this invention comprise a solid support and a ligand attached to the solid support. The ligand comprises a cyclic group which can be a monocyclic group or a polycyclic group, and a linking group that optionally comprises a sulphur atom. The ligand that attracts analytes through a mixed mode action, is attached to a solid support.

The ligand comprises a cyclic group, which can be a monocyclic or polycyclic group that is tethered to the solid support and that is substituted by a sulphate, sulphonate, phosphate, or phosphonate group. This monocyclic or polycyclic group can be an aromatic group, which, as defined here, is a cyclic hydrocarbon containing only unsaturated carbon-carbon bonds to give an aromatic system. While any aromatic group, in principle, may be employed in the present invention, a suitable aromatic group typically comprises one, two, or three aromatic rings. Thus, illustrative aromatic groups are phenyl and its substituted derivatives, such as tolyl and xylyl. Bicyclic aromatic groups comprise fused individual rings, and include but are not limited to naphthyl. Polycyclic aromatic groups include anthracenyl and phenanthrenyl, and groups such as acenanaphthylenyl that contain fused rings of different sizes. If an aromatic group is selected, it is preferred although not essential that the group be fused to a heterocyclic or heteroaromatic group, as described below.

A "heterocycle" is a saturated to partially saturated ring containing at least one hetero atom. Similarly, a "heteroaromatic group" is an aromatic group in which at least one carbon atom is substituted by a heteroatom. In the present invention, the hetero atom preferably is N, S, or O. It also is preferable that the heterocyclic or heteroaromatic group is a five- or six-member ring, as reagents that comprise these groups are readily and inexpensively obtained from commercial sources.

When a linking group, as defined below, does not contain ambivalent sulphur atom, then it is preferred that the heterocyclic or heteroaromatic group is one that establishes or contributes to the "thiophilic" character of the solid substrate, and is thus one that contains at least one S atom.

With the use of other linker groups that contain bivalent sulphur atoms, preferable heterocyclic or heteroaromatic groups may comprise at least one N atom, or combinations of S and N atoms.

Thus, exemplary heterocyclic or heteroaromatic groups include thiazoline, thiazolidone, imidazole, imidazoline, thiazole, triazoles, tetrazole, thiadiazole, imidazole, pyridine, and morpholine. In a particularly preferred embodiment, a suitable heterocyclic or heteroaromatic group is fused to an aromatic group, as described above. In this context, benzimidazole and benzothiazole are the readily available candidates, yielding superior solid substrates.

As mentioned above, the monocyclic or polycyclic group is substituted with a sulphate, sulphonate, phosphate, or phosphonate group. These groups are sufficiently acidic to exist as charged moieties within a large pH range, e.g., from about 2 to about 12. In this context, the solid support is ideally suited to adsorb biological substances such as immunoglobulins at physiological ionic strength and pH.

The term "substituted," as used herein, refers to the direct or indirect attachment of a sulphate, sulphonate, phosphate, or phosphonate group to the monocyclic or polycyclic group. Indirect attachment can occur through a spacer group, which is a $C_{1-6}$ straight or branched alkylene group. The alkylene group is optionally interrupted by one or more bivalent moieties that include but are not limited to —C(O)NH—, NHC(O)—, —O—, -S-, -S(O)—, -S(O)$_2$—, —NH—, —C(O)O—, and —OC(O)—. Thus, illustrative spacer groups include —CH$_2$—, —CH$_2$CH$_2$—, —CH$_2$—O—CH$_2$—, and —CH$_2$C(O)NHCH$_2$CH$_2$—.

The monocyclic or polycyclic group is tethered to the solid support by a linking group, which comprises a mercapto, ether, or amino containing moiety. Subject to structural considerations described below, it is preferred that the linking group is hydrophobic, thereby conferring hydrophobic character to the solid support at a pH where binding of a biological substance occurs through both electrostatic and hydrophobic interactions. Hydrophobic moieties include but are not limited to straight and branched $C_{1-6}$ alkylene groups, $C_{2-6}$ alkenylene groups, and $C_{2-6}$ alkynylene groups. Particularly useful moieties are ethylene and propylene. Other hydrophobic moieties comprise an aromatic group, as described above, to form, for example, phenethylene. The foregoing moieties are thus interrupted or capped by at least one mercapto, ether, or amino moiety. In embodiments where the monocyclic or polycyclic group does not comprise a sulphur atom, the linking group preferably contains a mercapto moiety. In this respect, the linking group confers hydrophobic and thiophilic characters to the solid substrate. One preferred mercapto-containing linking group is represented by the formula:

The hydrophobicity of the linking group can be readily tailored by introducing polar substituents, such as hydroxyl, a halide, or nitro; by oxidizing a mercapto moiety by known methods; by incorporating ether or amino moieties into the linking group; or combinations thereof. Thus, one such mercapto-containing linking group that is readily accessed is represented by the formula:

An illustrative amino-containing linking group is represented by the formula:

Preferably, the solid substrates comprised of amino-containing linking groups, or those containing oxidized mercapto moieties, also comprise monocyclic or polycyclic groups that comprise at least one S atom. In this respect, the solid substrate is able to retain some thiophilic character.

In another preferred embodiment, the linking group itself comprises a polysaccharide such as hydroxy-ethyl-cellulose, starch, amylose, or agarose. A preferred polysaccharide in this context is dextran. Thus, the solid support is modified with a polysaccharide, which can be derivatized with a linking group as described below.

Without limiting themselves to any particular theory, the inventors believe that the solid substrate of this invention operates via "mixed-modes" of interaction between the solid substrate and a biological substance. The aforementioned monocyclic and polycyclic groups have a pK-value below 4 and, hence, are negatively charged within the pH ranges of use as described above. A biological substance, such as an immunoglobulin, is contacted with the solid substrate between about pH 4 and pH 6, in which range the biological substance bears a net positive or neutral charge. In this pH range, the biological substance binds to the solid substrate through one or more types of interactions with the mono or polycyclic groups. The interactions include coulombic attractions and mild hydrophobic associations. When the pH is raised above about 8, the biological substance gains a net negative charge, thereby creating electrostatic repulsion between the negatively charged solid substrate and the negatively charged biological substance. Consequently, the biological substance is released by the electrostatic repulsion from the solid substrate and can then be isolated. It is believed that these repulsive ionic forces are greater than the weaker attractive forces noted above.

Solid Substrate

This invention contemplates a solid support to which the mixed mode ligand is attached. Two different formats are contemplated in particular. In one format, the solid support is of the form typically used for chromatography media, that is, a bead or particle. These beads or particles are derivatized with the mixed mode ligand. The beads or particles form a chromatography medium that one can use to pack the column. In another format, the solid support takes the form of a chip, that is, a solid support having a generally planar surface to which the mixed mode ligand can be attached, covalently or otherwise. Chips that are adapted to engage a probe interface of a detection device are also called "probes."

Beads and Particles

In accordance with the teachings of this invention, the solid substrate first comprises a solid support, which may comprise an organic material. Exemplary organic materials are polysaccharides, such as cellulose, starch, agar, agarose, and dextran. Hydrophilic synthetic polymers are contemplated, including substituted or unsubstituted polyacrylamides, polymethacrylamides, polyacrylates, polymethacrylates, polyvinyl hydrophilic polymers, polystyrene, polysulfone, and copolymers or styrene and divinylbenzene. Alternatively, inorganic materials may be used as the solid support material. Such inorganic materials include but are not limited to porous mineral materials, such as silica; hydrogel containing silica, zirconia, titania, alumina; and other ceramic materials. It is also possible to use mixtures of these materials, or composite materials formed by copolymerization of or by an interpenetrated network of two materials, such as those disclosed in U.S. Pat. No. 5,268,097, U.S. Pat. No. 5,234,991, and U.S. Pat. No. 5,075,371.

The solid support may be in the form of beads or irregular particles of about 0.1 mm to about 1,000 mm in diameter. Alternatively, the solid support can be fashioned into fibres, membranes, or sponge-like materials permeated with holes in the micron to multi-millimeter sizes.

The monocyclic or polycyclic groups described above are chemically immobilized on the solid support by forming covalent bonds between the solid support and the linking group, and between the linking group and monocyclic or polycyclic groups. In typical scenarios, the solid support is first treated with a bifunctional reagent which serves to introduce onto the solid support reactive groups that form part or the entire linking group. For some solid supports, such as cellulose, composites containing a hydrogel, or other materials presenting hydroxyl groups, it is often advantageous to deprotonate the hydroxyl groups with a hydroxide source, for example, prior to reaction with a bifunctional reagent. The bifunctional reagent is capable of reacting both with the solid support and with reagents that contain the monocyclic or polycyclic groups. Illustrative bifunctional reagents, which contain the same or different functional groups, include but are not limited to epichlorhydrin, epibromhydrin, dibromo- and dichloropropanol, dibromobutane, ethylene glycol diglycidylether, butanediol diglycidylether, divinyl sulfone, allylglycidylether, and allyl bromide.

Once functionalized, the solid support is then washed extensively with one or more solvents to remove unreacted bifunctional reagent, reaction byproducts, or both. A typical solvent used in this regard is water.

The monocyclic or polycyclic groups then are introduced by way of reagents that contain such groups substituted with mercapto, hydroxyl, or amino groups. Such reagents react with functional groups presented by the functionalized solid support as described above.

The particular pairing of a bifunctional reagent with a monocyclic or polycyclic reagent is guided by well-known chemistries. For example, solid supports that are functionalized with epoxides may undergo reactions with mercapto, hydroxy, or amino-containing reagents to furnish a substrate with ethylene-containing linking groups. Other solid supports modified with allyl bromide, for example, present alkene groups that can be reacted directly with mercapto-containing reagents. Alternatively, the alkene groups can be further brominated to furnish suitably reactive brome derivatives.

The concentration of immobilized monocyclic or polycyclic group can vary between a fraction of a micromole to several hundred micromoles per milliliter of solid support, depending upon the concentration of bifunctional reagent used to make the solid support.

Low concentrations of the immobilized group typically result in low separation capacity of the solid substrate, whereas high concentrations generally lead to increased capacity.

As described above there are several advantages having a $PrP^{SC}$ removal resin which mainly does not bind to the $PrP^{SC}$ one being that it is possible to extensively wash the resin with different buffer compositions before eluting the product, which makes it possible to at least reduce the number of $PrP^{SC}$ of even different biochemical composition to a very low level or remove $PrP^{SC}$ from the composition. For example it is possible to wash the resin with different types of wash buffers, including high respectively low salt buffers to interrupt ionic respectively hydrophobic interaction in which smaller amount of the prions can be binding towards the resin or even the product, before eluting the product. Detergents, alcohols and amino acids are also examples, which can be added to the washing buffers to achieve an optimal purity before eluting the product. It is significant more difficult to perform similar washing step to other types of "standard" chromatography media like for examples different types of ion exchange resins where the $PrP^{SC}$ binds to the resin. Even if the binding affinity is significant higher compared to product there will always be a risk that $PrP^{SC}$ to some degree will co-elute from the resin together with the product. Therefore there is a big advantage of using a resin in which the product "multimodal" binds to the resin whereas $PrP^{SC}$ have a relatively low affinity to the resin, which makes it possible to apply appropriate washing steps before eluting the product.

According to the invention the target protein is eluted after $PrP^{SC}$ elution e.g. by amending the ionic strength of the elution buffer by increasing or decreasing the ionic strength, adding alcohols to the elution buffer—in particular in aqueous solution—such as mono- or dihyroxyalkanols, e.g. lower aliphatic alcohols such as methanol, ethanol, propanol, and/or amending the pH-value of the elution buffer by increasing or decreasing the pH.

Also a combination of the described elution techniques can be employed. E.g. the invention uses increased ionic strength and increased ethylene glycol amount.

Also other elution conditions can be used, such as increased concentration of aminoacids, increased concentrations with specific salts according to "hofmeister serie".

The elution of the target protein depends on the biochemical property of the target protein. For example it is possible to use the co-enzyme of the target protein or other substances with a high recognition towards the tertial structure of the target protein, e.g. antithrombin as target protein which elutes with an increased concentration of heparin.

The prion protein reduction value in the protein fraction comprising the target protein is >1 to 4 lg(10), as calculated from the amount which was initially applied to the resin. The prion analytical value in the protein fraction of interest is below detection limit of the prion Western blot assay.

In an embodiment of the present invention the chromatographic conditions comprise at least two of the following steps:

i) Employing a loading and equilibration buffer containing a solvent and/or a non-ionic detergent;

ii) Employing a wash buffer without a solvent and/or non-ionic detergent;

iii) Employing a wash buffer containing an alcohol and/or an amino acid;

iv) Employing a wash buffer containing a high salt concentration;

v) Employing a wash buffer containing a low salt concentration;

vi) Employing a buffer containing a combination of alcohol and high salt concentration.

In a further embodiment of the present invention the chromatographic conditions comprise at least two of the following steps:

i) Employing a loading and an equilibration buffer containing a solvent and or a non-ionic detergent;

ii) Employing a first wash buffer which is a buffer without a solvent and a non-ionic detergent;

iii) Employing a second wash buffer containing an alcohol and an amino acid;

iv) Employing a third wash buffer containing high salt concentration;

v) Employing a fourth wash buffer containing low salt concentration;

vi) Employing an elution buffer containing a combination of an alcohol and high salt concentration.

In yet another embodiment of the invention the buffers employed are as follows i) Loading and equilibration buffer contain tri-n-butylphosphate and/or TRITON x-100 (detergent) in a concentration ranging of from about 0.1 to about 10% (w/w);

ii) The second wash buffer contains ethylene glycol and/or lysine/arginine ranging of from about 5 to about 30% (w/w) of ethylene glycol and of from 0.2 to about 1.5 M lysine/arginine;

iii) The third wash buffer contains sodium chloride in a concentration ranging of from about 0.5 to about 4 M, in particular of from about 0.5 to about 1.5 M;

iv) The fourth wash buffer contains sodium chloride in concentration ranging of from about 0.01 to about 0.2, in particular 0.01 to about 0.1 M;

v) The elution buffer contains ethylene glycol and/or sodium chloride ranging in concentration of from about 25 to about 75% (w/w), in particular of from about 25 to about 50% of ethylene glycol and of from about 0.5 to about 4 M NaCl.

In a further embodiment of the present invention the chromatographic conditions comprise at least two of the following steps:
i) Loading and equilibration buffer contain tri-n-butylphosphate and/or TRITON x-100 (detergent) in a concentration ranging from 0.3-5% (w/w);
ii) Washing with >10 column volumes of a second wash buffer containing ethylene glycol and/or lysine/arginine ranging from 10-25% (w/w) of EG and 0.3-1.0 M lysine/arginine;
iii) Washing with >10 column volumes of a third wash buffer containing sodium chloride in a concentration ranging from 0.8-1.5 M;
iv) Washing with >10 column volumes of a fourth wash buffer containing sodium chloride in concentration ranging from 0.03-0.15 M;
v) The elution buffer contains ethylene glycol and/or sodium chloride ranging in concentration from 35-65% (w/w) for EG and 0.8-3.0 NaCl.

In another embodiment of the invention the buffers employed are as follows
i) Loading and equilibration buffer contain tri-n-butylphosphate and/or TRITON x-100 (detergent) in a concentration ranging from 0.8-1.2% (w/w);
ii) Washing with >20 column volumes of a second wash buffer containing ethylene glycol and/or lysine/arginine ranging from 18-22% (w/w) of EG and 0.4-0.6 M lysine/arginine;
iii) Washing with >20 column volumes of a third wash buffer containing sodium chloride in a concentration ranging from 0.8-1.2 M;
iv) Washing with >20 column volumes of a fourth wash buffer containing sodium chloride in a concentration ranging from 0.08-0.12 M;
v) The elution buffer contains ethylene glycol and/or sodium chloride ranging in concentration from 45-55% (w/w) for EG and 1.3-1.7 NaCl.

The advantage of applying washing buffers of different types is that this increases the possibility that prions of different types and which binds due to to different interactions to the resin or the target protein, can be removed. Also by increasing the amount of respectively washing buffer (i.e one column volume is equal to the volume of the resin) the security of any remaining prions "slowacting" on the buffer applied, can be increased.

The multimodal chromatographic material may contain
i) a positive charged N-Benzyl-N-methyl ethanolamine ligand;
ii) a negatively charged 2-(benzoylamino) butanoic acid ligand; iii) a phenylpropyl ligand;
iv) a N-hexyl ligand;
v) a 4-Mercapto-Ethyl-Pyridine ligand;
vi) a 3-[{3$^{31}$ methyl-5-((tetrahydrofuran-2-ylmethyl)amino)-phenyl}amino]benzoic acid ligand.

Subject matter of the present invention is also a prion protein depleted fraction of a protein isolated from potentially infectious protein containing sources. The fraction contains pharmaceutically applicable proteins obtainable according to the method of the invention.

In particular protein fractions are claimed comprising plasma proteins, peptide hormones, growth factors, cytokines and polyclonal immunoglobulins proteins, plasma proteins selected from human and animal blood clotting factors including fibrinogen, prothrombin, thrombin, prothrombin complex, FX, FXa, FIX, FIXa, FVII, FVIIa, FXI, FXIa, FXII, FXIIa, FXIII and FXIIIa, von Willebrandt factor, transport proteins including albumin, transferrin, ceruloplasmin, haptoglobin, hemoglobulin and hemopexin, protease inhibitors including β-antithrombin, α-antithrombin, α2-macroglobulin, Cl-inhibitor, tissue factor pathway inhibitor (TFPI), heparin cofactor II, protein C inhibitor (PAI-3), Protein C and Protein S, α-1 esterase inhibitor proteins, α-1 anti-trypsin, antiangionetic proteins including latent-antithrombin, highly glycosylated proteins including α-1-acid glycoprotein, antichymotrypsin, inter-α-trypsin inhibitor, α-2-HS glycoprotein and C-reactive protein and other proteins including histidine-rich glycoprotein, mannmman binding lectin, C4-binding protein, fibronectin, GC-globulin, plasminogen, blood factors such as erythrmopoeitin, interferon, tumor factors, tPA, γCSF.

The invention is further described by the following non-limiting examples.

EXAMPLES

Example 1

Column and Resin

Tricorn column (GE Healthcare, Sweden, cross sectional area: 0.2 cm$^2$, diameter 0.5 cm) was packed with Capto MMC resin (GE Healthcare Cat. No. 17-5317-10, lot No. 308581), 9 cm bed height, Column volume: 1.8 ml.
Starting Material
A mixture of recombinant derived proteins from HEK 293 cells and concentrated over a capture column step, was used as starting material (batch number: BPP 047 SP eluate, 117 μg protein/ml).
Buffer Compositions*
*The buffers were prepared as in relation to 1 kg of Water added instead of 1 L as a final volume. This will have a small impact on final molarities, since additives will increase the final volume slightly.
Buffer 1 (Equilibration Buffer with S/D Added)
 0.3 M NaCl, 0.01 M CaCl$_2$ (2×H$_2$O), 0.01 M L-Histidin, 1% w/w TRITON x-100 (detergent), 0.3% w/w TNBP, pH: 7.0±0.1, Conductivity: 29±3 mS/cm$^2$ at +25° C. Buffer 2 (Equilibration Buffer Without S/D)
 0.3 M NaCl, 0.01 M CaCl$_2$ (2×H$_2$O), 0.01 M L-Histidin, 0.02% (w/w) TWEEN 80 (detergent), pH: 6.5±0.1, Conductivity: 31±3 mS/cm$^2$ at +25° C.
Buffer 3 (Wash 1; Lysin & Ethyleneglycol (=EG))
 0.3 M NaCl, 0.01 M CaCl$_2$ (2×H$_2$O), 0.01 M L-Histidin 0.02% (w/w) TWEEN 80 (detergent), 0.5 M L-Lysin monochlorid, 20% (w/w) Ethylene glycol (=EG)
 pH: 6.5±0.1, Conductivity: 37±3 mS/cm$^2$ at +25° C.
Buffer 4 (Wash 2; High Salt Wash)
 1.0 M NaCl, 0.05 M CaCl$_2$ (2×H$_2$O), 0.05 M L-Histidin, 0.02% (w/w) TWEEN 80 (detergent), pH: 6.5±0.1, Conductivity: 89±5 mS/cm$^2$ at +25° C.
Buffer 5 (Wash 3; Low Salt Wash)
 0.1 M NaCl, 0.01 M CaCl$_2$ (2×H$_2$O), 0.01 M L-Histidin, 0.02% (w/w) TWEEN 80 (detergent) pH: 6.5±0.1, Conductivity: 13±3 mS/cm$^2$ at +25° C.
Buffer 6 (Elution Buffer)
 1.5 M NaCl, 0.02 M CaCl$_2$ (2×H$_2$O), 0.02 M L-Histidin, 0.02% (w/w) TWEEN 80 (detergent) 50% (w/w) Ethylene glycol (EG), pH: 6.5±0.1 (adjust the pH before addition of EG)
 Conductivity: 39±3 mS/cm$^2$ at +25° C., measured after addition of EG.
Buffer 7 (Regeneration buffer)
 1M Sodium Hydroxide
For pH Adjustment:
 1 M HCl Chromatography conditions:

TABLE 1

Outlining the approximate amounts of buffer applied, flow rates expressed as ml/min as well as cm/hour.
Time required for each buffer step and contact time with the gel for the protein solution is also shown.
Capto MMC run
Column volume = (ml) 1.8

| Block | No. CV | ml | Flow ml/min | Flow cm/h | Time (min) | Contact time (min) |
|---|---|---|---|---|---|---|
| Equilibration buffer + SD | 5 | 9 | 1.00 | 306 | 9 | 1.8 |
| Sample feed | 27 | 48 | 1.00 | 306 | 48 | 1.8 |
| Equilibration – SD | 10 | 18 | 1.00 | 306 | 18 | 1.8 |
| Lysin + EG wash | 20 | 35 | 0.60 | 183 | 59 | 2.9 |
| High salt wash | 10 | 18 | 1.00 | 306 | 18 | 1.8 |
| Low salt wash (start upflow) | 5 | 9 | 1.00 | 306 | 9 | 1.8 |
| Elution buffer, 1.5M NaCl | 7 | 12 | 0.20 | 61 | 62 | 8.8 |

MMC resin, packed in a Tricorn column with a bed height of approx. 9 cm. The chromatography step was monitored for conductivity and at 280 nm. The protein load was approximately 3 mg related to 1 ml of resin.

First, the column was properly equilibrated with equilibration buffer containing S/D chemicals until a stable base line was obtained. The starting material was added S/D chemicals at a ratio of 14 g S/D stock per kg to obtain the same concentration as the equilibration buffer, this was stirred for at least 10 minutes before application of the protein solution to the column. Fractions of the following buffers where collected and analysed for total protein (and prions in the $PrP^{SC}$ spiking experiments) The chromatography profile measured at an absorbance of 280 nm can be seen in appendix 2:

Flow through (Buffert 1+proteins)

Buffer 1 (High non-ionic detergent Buffer; 0.3 M NaCl, 0.01 M $CaCl_2$, 0.01 M L-Histidin, 1% w/w TRITON x-100 (detergent), 0.3% w/w TNBP, pH: 7.0)

Buffer 2 (Low non-ionic detergent Buffer; 0.3 M NaCl, 0.01 M $CaCl_2$, 0.01 M L-Histidin, 0.02% (w/w) TWEEN 80 (detergent) pH 6.5)

Buffer 3 (Amino acid/Alcohol Buffer; 0.3 M NaCl, 0.01 M $CaCl_2$, 0.01 M
L-Histidin, 0.02% (w/w) TWEEN 80 (detergent), 0.5 M L-Lysin monochlorid, 20% (w/w) Ethylene glycol, pH 6.5)

Buffer 4 (High salt Buffer; 1.0 M NaCl, 0.05 M $CaCl_2$, 0.05 M L-Histidin, 0.02% (w/w) TWEEN 80 (detergent), pH: 6.5)

Buffer 5 (Low salt Buffer; 0.1 M NaCl, 0.01 M $CaCl_2$, 0.01 M L-Histidin, 0.02% (w/w) TWEEN 80 (detergent) pH: 6.5)

Buffer 6 (High salt/High Alcohol Buffer) 1.5 M NaCl, 0.02 M $CaCl_2$, 0.02 M L-Histidin, 0.02% (w/w) TWEEN 80 (detergent), 50% (w/w) Ethylene glycol (EG), pH: 6.5

Buffer 7 (Regeneration Buffer; 2M NaCl)

The column was regenerated with 20 column volumes of 1 M NaOH and stored in 20% (v/v) ethanol for further use.

Results

TABLE 2

(Detection of total Protein in experiment without prions)

| Sample | Sample volume (ml) | Total Protein ug/ml | Total Protein mg | Total Protein % |
|---|---|---|---|---|
| Starting material (Load sample) | 47 | 117 | 5.5 | 100 |
| Flow through (Buffer 1) | 40 | na | na | na |
| Buffer 2 | 20 | na | na | na |
| Buffer 3 | 40 | 17.9 | 0.7 | 13% |
| Buffer 4 | 20 | 10.7 | 0.2 | 4% |

TABLE 2-continued (Detection of total Protein in experiment without prions)

| Sample | Sample volume (ml) | Total Protein ug/ml | Total Protein mg | Total Protein % |
|---|---|---|---|---|
| Buffer 5 | 10 | 13.6 | 0.1 | 2% |
| Buffer 6 | 9 | 150 | 1.4 | 25% |
| Buffer 7 | 18 | na | na | na | na = Not analysed due to interference of buffer with total protein analytical method Example 2

Prion Spiking Experiment

To be able to determine the prion protein removal of the chromatography procedure described in example 1, a prion spiking experiment was performed. The same column, resin, buffers and starting material as in Example 1 was used.

Prion Protein Infectivity Starting Material

A microsomal/cytosolic fraction of the 263K strain of hamster adapted scrapie was used in this experiment.

Approximately 54 g of the protein start material (the same as in example 1; batch number: BPP 047 SP eluat) containing 117 ug/ml protein, were thawed in a waterbath at 25° C. and warmed up to a temperature of 24.0° C. (target: 20-25° C.). 51.12 g (target: 50±2 g) of start material were then weighed and spiked with 2.6 ml (target: 2.5±0.2 ml) microsomal/cytosolic fraction to a final concentration of 5.1%. pH of the spiked start material was checked to be 6.994 (target: 7.0±0.1). A 6 ml aliquot was then removed, aliquotted and stored at −60° C. (sample spiked start material—SSM).

1.955 g of TRITON x-100 (detergent) were mixed with 0.582 g of TnBP (target ratio: 10 parts+3 parts, determination per weight) and stirred for 36 min. 0.665 g of the S/D reagent were then immediately added to the remaining 47.72 g of spiked start material (target ratio: 14 g S/D-reagent per kg of spiked start material) and stirred for 31 min. The temperature of the start material was checked to be 24.5° C. in the beginning and 23.7° C. at the end of the stirring phase (target range: 18-25° C.).

Chromatography Step

A GE Healthcare Tricorn 1.8 ml column packed with Capto MMC resin (CV=1.0 ml, bed height=9 cm) was equilibrated with 8.3 CV of Buffer 1 (Equilibration buffer with S/D) at a flow rate of 1.0 ml/min (target: 5 CV at 1.0 ml/min). 47.29 g of S/D treated spiked start material were then loaded onto the column, applying a flow rate of 1.0 ml/min (target: 45±2 g at 1.0 ml/min). Following loading, the column was flushed with 10.0 CV of Buffer 2 (Equilibration Buffer without S/D) at a flow rate of 0.8 ml/min (target: 10 CV at 1.0 ml/min). Collection of the flow through started when the UV signal began to rise and was continued until the absorbance started to drop. The weight of the flow through fraction was determined (actual weight: 48.23 g), a 16 ml aliquot removed, aliquoted and stored at −60° C. (sample flow through-FT). Wash fraction 1 was collected during flushing with Buffer 2. The actual weight of this fraction was determined to be 12.75 g and a 12 ml aliquot was removed and stored at −60° C. (sample wash1-W1).

The column was then washed with 22.2 CV of Buffer 3 (Lysin & Ethylen glycol wash) at a flow rate of 0.6 ml/min (target: 20 CV at 0.6 ml/min). During washing with Buffer 3, wash fraction 2 was collected and the actual weight of this fraction determined to be 40.35 g. A 16 ml aliquot was removed, and stored at −60° C. (sample wash2-W2).

During washing the column with 10.0 CV of Puffer 4 (High Salt Wash) at a flow rate of 0.9 ml/min (target: 10 CV at 1.0 ml/min), wash fraction 3 was collected. An actual weight of 18.48 g was determined, a 16 ml aliquot was then removed, aliquoted and stored at ≤−60° C. (sample wash3-W3).

During washing the column with 5.0 CV of Buffer 5 (Low Salt Wash) at a flow rate of 1.0 ml/min (target: 5 CV at 1 ml/min), wash fraction 4 was collected. The actual weight of this fraction was determined to be 12.22 g. A 11.5 ml aliquot was removed and stored at −60° C. (sample wash4-W4).

The product was then eluted with 8.3 CV of Buffer 6 (Elution Buffer), applying a flow rate of 0.2 ml/min (target: 7 CV at 0.2 ml/min). Collection of the eluate was carried out during the whole period of flushing the column with Buffer 6. The actual weight of the eluate fraction was determined to be 13.54 g, a 12.5 ml aliquot was removed and stored at ≤−60° C. (sample eluate-E).

During regeneration of the column with 9.4 CV of Buffer 7 (Regeneration Buffer) at a flow rate of 0.6 ml/min (target: 20 CV at 0.6 ml/min), the regeneration fraction was collected. An actual weight of 17.97 ml was determined, a 16 ml aliquot removed and stored at −60° C. (sample regenaration—Reg).

TABLE 3

(Result of prion spiking experiment)

| Sample | Sample volume (ml) | PrP$^{SC}$ Content Log$_{10}$ | PrP$^{SC}$ Content % |
|---|---|---|---|
| Starting material (sample-SSM). | 54 | 4.67 | 100 |
| Flow through, Buffer 1 (sample-FT) | 48 | 4.68 | 102 |
| Buffer 2 (sample-W1). | 13 | 3.61 | 9.5 |
| Buffer 3 (sample-W2) | 40 | 2.61 | 0.9 |
| Buffer 4 (sample-W3) | 18 | <1.27 | <0.04 |
| Buffer 5 (sample-W4) | 12 | <1.09 | <0.03 |
| Buffer 6 (sample-E) | 14 | <1.13 | <0.03 |
| Buffer 7 (sample-Reg) | 18 | <1.26 | <0.04 |

Discussion

As can be seen from Table 3 and appendix 1 (FIG. 1-5) excellent prion protein removal values can be seen for Buffer 4-7 fractions. Thus protein products, which elutes within these fractions would have very good safety margins in regard of PrP$^{Sc}$ removal. What is also very important is that the mass balance of the applied prion protein indicates that no PrP$^{Sc}$ at all are to be found in other fractions than the flow through and early washing buffer. To our knowledge, this has not been shown previously in prior art. In the published examples of chromatography resins as prion protein removal step, even if relatively acceptable prion protein reduction values are achieved, prion proteins can normally be found in several fractions, both before and after taking care of the product fraction, indicating a risk of cross over contamination.

Description of Analysis

Determination of Total Protein According to Bradford

Protein determination according to Bradford is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible colour change. The assay is useful since the extinction coefficient of a dye-albumin complex solution is constant over a 10-fold concentration range. See for further information also Bradford, MM. A rapid and sensitive for the quantitation of microgram quantities of protein utilizing the principle of protein-dye binding. *Analytical Biochemistry* 72: 248-254. 1976.

Western Blot Assay for the Detection of PrP$^{SC}$

The Western blot assay is a semi-quantitative determination of proteinase K resistant Scrapie associated prion protein (PrP$^{SC}$).

The Western blot assay was performed as described by D C Lee et al., Journal of Virological Methods 2000; 84:77-89.

The invention claimed is:

1. A chromatography process for decontaminating a target protein of infectious proteins (PrP$^{SC}$) comprising the steps of contacting a potentially PrP$^{SC}$-contaminated sample of HEK 293 cell-derived proteins containing the target protein with a multimodal chromatographic material, wherein the multimodal chromatographic material comprises a negatively charged 2-(benzoylamino) butanoic acid ligand,
setting buffer conditions so that the target protein binds and the PrP$^{SC}$ do not bind to the negatively charged 2-(benzoylamino) butanoic acid ligand by sequentially
i) employing a pH 7.0±0.1 loading and equilibration buffer containing at least one of tri-n-butylphosphate and octoxynol (TRITON X-100) in a concentration ranging of from 0.1 to 10% (w/w),
ii) employing a pH 6.5±0.1 wash buffer without tri-n-butylphosphate and/or octoxynol (TRITON X-100), and
iii) employing a pH 6.5±0.1 wash buffer containing 5 to 30% (w/w) of at least one of ethylene glycol and 0.2. to 1.5 M lysine/arginine, and then
eluting the target protein from the negatively charged 2-(benzoylamino) butanoic acid ligand,
to obtain the target protein in a PrP$^{SC}$ decontaminated fraction of HEK 293 cell-derived proteins.

2. The method of claim 1 wherein the target protein is eluted with an elution buffer by
i) increasing or decreasing the ionic strength of the elution buffer,
ii) adding one or more alcohols to the elution buffer, and/or
iii) increasing or decreasing the pH of the elution buffer.

3. The method of claim 1 wherein the PrP$^{SC}$ removal value in the fraction containing the target protein is >1 to 4 log(10), as calculated from the amount which was initially applied to the resin.

4. The method of claim 1 wherein the PrP$^{SC}$ analytical value in the protein fraction of interest is below detection limit of the prion Western blot assay.

* * * * *